United States Patent [19]

Siegmund

[11] Patent Number: 4,919,112

[45] Date of Patent: Apr. 24, 1990

[54] LOW-COST SEMI-DISPOSABLE ENDOSCOPE

[75] Inventor: Walter P. Siegmund, Windham, Conn.

[73] Assignee: Schott Fiber Optics, Southbridge, Mass.

[21] Appl. No.: 334,335

[22] Filed: Apr. 7, 1989

[51] Int. Cl.$^5$ ............................................... A61B 1/00
[52] U.S. Cl. ............................................. 128/4; 128/6
[58] Field of Search ................................... 128/4, 6, 7

[56] References Cited

U.S. PATENT DOCUMENTS

| | | | |
|---|---|---|---|
| 3,373,736 | 3/1968 | Fiore et al. | 128/6 |
| 4,146,019 | 3/1979 | Bass et al. | 128/6 |
| 4,188,942 | 2/1980 | Fehlberg | 128/6 |
| 4,624,243 | 11/1986 | Lowery et al. | 128/6 |
| 4,736,733 | 4/1988 | Adair | 128/6 |

Primary Examiner—William H. Grieb
Attorney, Agent, or Firm—Bachman & LaPointe

[57] ABSTRACT

An endoscope is disclosed having a separable, disposable shaft where a push-pull mechanism, housed in liquid tight fashion in a control handle unit, is operable to actuate a shaft flexure means within the shaft effective deflect the distal end of the shaft.

18 Claims, 2 Drawing Sheets

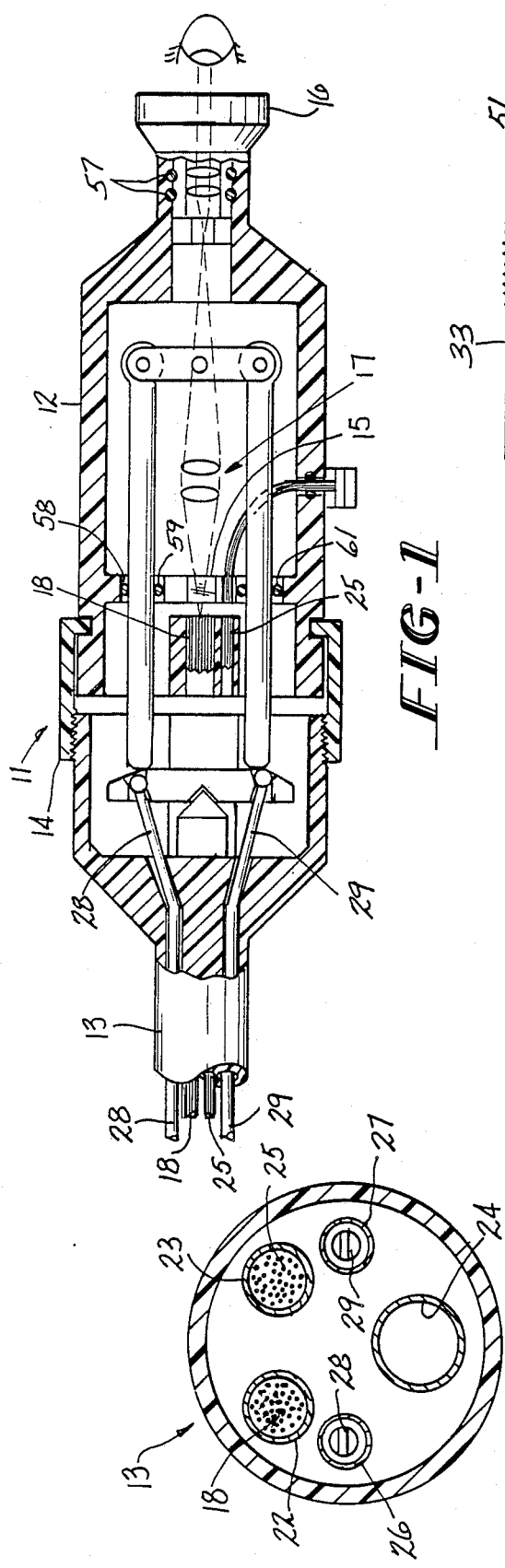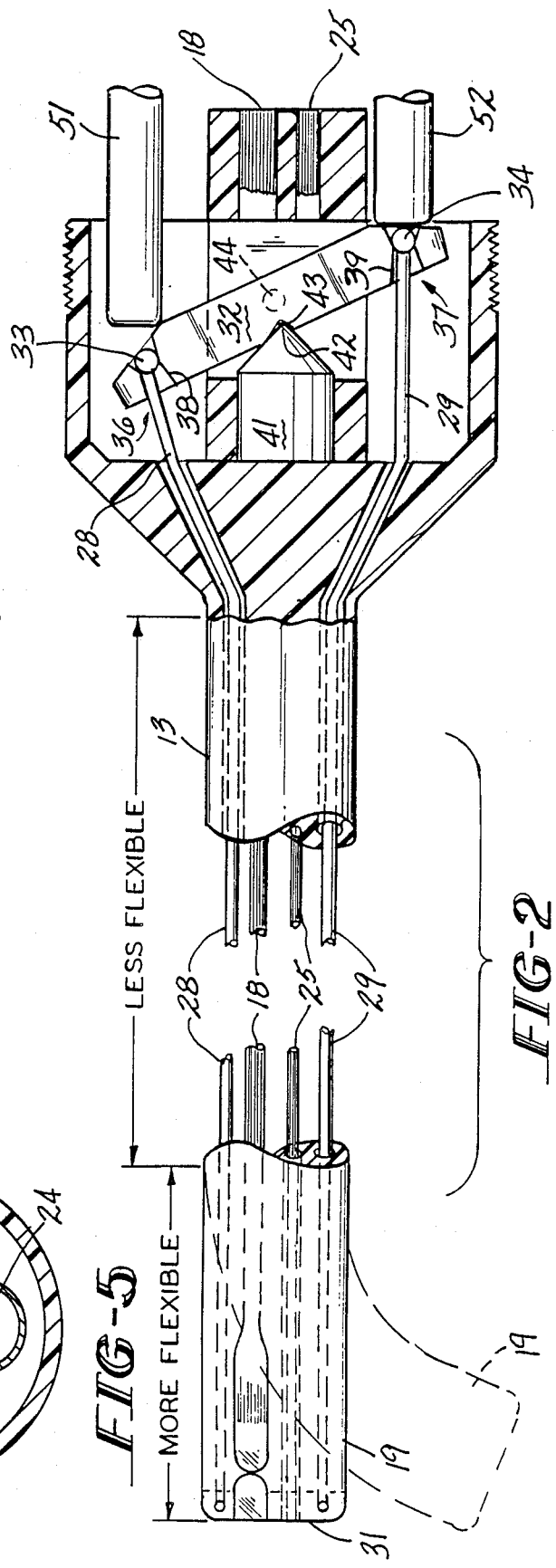

LOW-COST SEMI-DISPOSABLE ENDOSCOPE

BACKGROUND OF THE INVENTION

The present invention relates to endoscopes and relates, in particular, to endoscopes having a control handle unit and a separable, disposable, flexible shaft unit.

It is usual and customary to include in the overall endoscope structure conduits or channels for air, vacuum, fiber optic image and light bundles including channels for mechanical instruments for obtaining biological samples.

In addition, it is desirable to provide means in the shaft operable via the control handle unit to flex the shaft, in particular, the distal end of the shaft.

In the situation where the shaft is disposable, several problems are encountered.

First, it is difficult to devise an operable, inexpensive shaft unit flexure means where one can afford to dispose of the portion of the flexure means contained in the shaft.

Second, it is desirable to design the control handle unit in watertight fashion so that the unit can be immersed in cleansing fluid without contaminating the interior of the handle unit.

BRIEF DESCRIPTION OF THE INVENTION

Consequently, it is a primary feature of the present invention to provide an endoscope having an inexpensive, disposable, flexible shaft unit and a fluid tight control handle unit where the distal end of the shaft unit is flexed under control of the handle unit.

A further feature of the invention is the provision of novel flexure means in the shaft unit.

A further feature of the invention is the provision of novel means in the control handle unit for driving the shaft flexure means while preserving the disposable character of the shaft unit.

A further feature of the invention is the placement of power means in the handle unit and the placement of shaft flexure means in the shaft unit so that mere areal, surface contact between elements of the power means and the shaft flexure means is adequate to complete a driving connection.

It is a still further feature of the invention to provide a quick operating connection between the shaft unit and the handle unit such as an interrupted thread or a bayonet connection.

A further feature of the invention is the provision of seal means about the eyepiece and all movable elements projecting from the handle unit to make the interior of the handle unit watertight and to facilitate immersing the handle unit into a cleansing bath without contaminating the interior of the handle unit.

It is a further feature of the invention to provide a novel and inexpensive method of arranging the handle and the shaft unit so that the shaft unit is articulable and disposable.

An endoscope embracing certain features of the invention may comprise a control handle means, a flexible shaft means, quick operating connection means for fastening the shaft means to the handle means releasably, shaft articulation means within said shaft means and power means in said handle means for driving said shaft articulation means whereby elements of said power means and said shaft articulating means make mere areal, surface contact when the handle means and the shaft means are connected.

A method for making a disposable, flexible endoscope shaft unit articulable economically embracing certain other principles of the invention may comprise the steps of providing a control handle unit, providing a disposable, flexible shaft unit separable from said control handle unit, placing shaft flexure means in the shaft unit, placing power means for driving the shaft flexure means in the handle unit and positioning the power means and the shaft flexure means in their respective units so that when the units are connected the power means makes areal, surface contact with the flexure means effective to drive the flexure means.

Other features and advantages of the present invention will become more apparent from an examination of the succeeding specification when read in conjunction with the appended drawings, in which:

BRIEF DESCRIPTION OF THE DRAWINGS

FIG. 1 is a sectional view of a portion of an IU endoscope showinq a disposable, flexible shaft unit connected to a control handle unit;

FIG. 2 is a sectional view of the flexible, disposable shaft end of the endoscope, enlarged, showing the push rods of the handle unit actuating the shaft flexure means;

FIG. 5 is a sectional view, enlarged, of the shaft showing typical shaft channels.

DETAILED DESCRIPTION OF THE INVENTION

Figure 3:
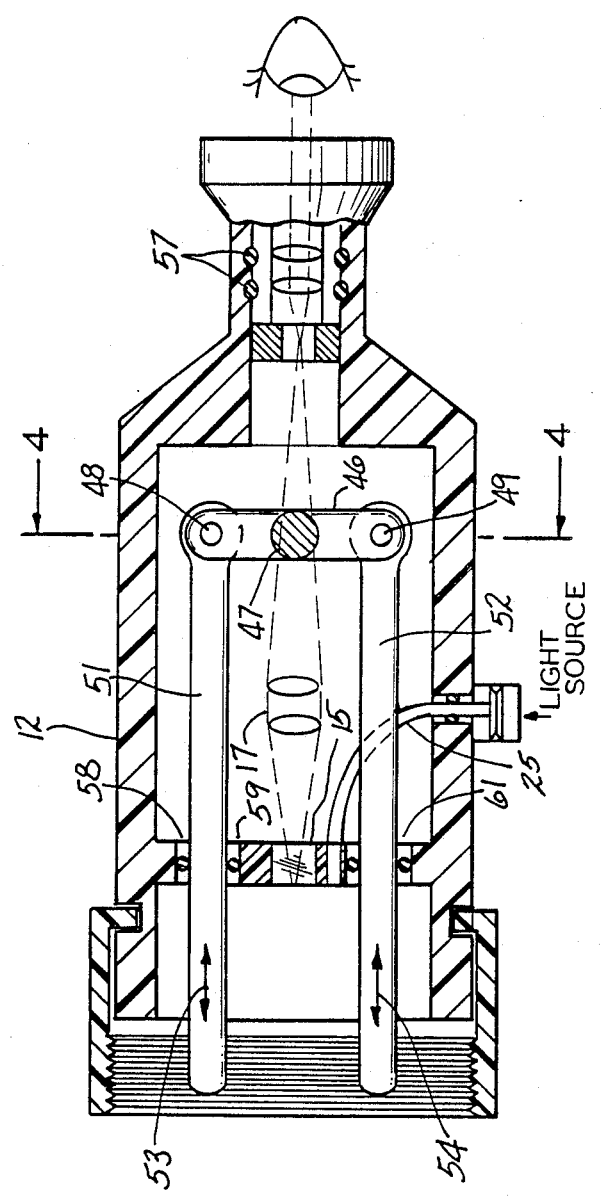
FIG. 3 is a sectional view of the handle unit showing the push rods in an equilibrium position.

Referring in detail to the drawings, the reference numeral 11 designates an endoscope having a control handle unit 12 and a separable, flexible, disposable shaft unit 13 threadably connected as at 14.

The connection 14 is a quick operating connection and can take the form of interrupted threads as in the breech lock of a firearm, a bayonet connection or other suitable connection device. The type of connection is not critical to the invention so long as it is quick operating and reliable.

An eyepiece 16 in conjunction with suitable optics 17 and sealed transfer plate 15 cooperate with a fiber optic image bundle 18 for observing an object at the distal end 19 (FIG. 2) of shaft unit 13 in the usual and customary fashion.

The shaft may take the form of an extrusion. It is also desireable to fabricate a portion of the shaft unit, near the diatal end 19, of a material that is more flexible than the flexibility of the main body of the shaft (as indicated in FIG. 2) to facilitate deflection of the distal end.

As is most apparent in FIG. 5, the shaft unit 13 includes channels or conduits 22 for the image bundle, 23 for the fiber optics light bundle 25, 24 for suction, liquid and air and channels 26 and 27 for strand means or control wires 28 and 29.

The control wires 28 and 29 form a part of the shaft flexure (deflection) means as will become more apparent as the specifications proceeds.

One end of each control wire 28–29 is fixed to a face place 31 at the distal end 19 of the shaft 13 and each opposite end is fixed to a rocker arm or cross head 32 as indicated by the beads or wire heads 33 and 34.

The wires are received in through slots 36 and 37 formed in the extremities of the rocker arm 32 and the slots have an inwardly, bevelled sides 38 and 39 to provide adequate clearance for the control wires as the rocker arm pivots about fixed fulcrum 41 as is most apparent in FIG. 2.

The rocker arm, in the embodiment shown in FIG. 2, is retained on the fulcrum 41 by light tension in the control wires 28 and 29 and by the engagement of apex 42 of the fulcrum and notch 43 in the rocker arm.

In some alternative embodiments, it may be necessary to provide a hinge pin as indicated in dashed lines at the reference numeral 44 (FIG. 2) to stabilize the rocker arm.

Figure 4:
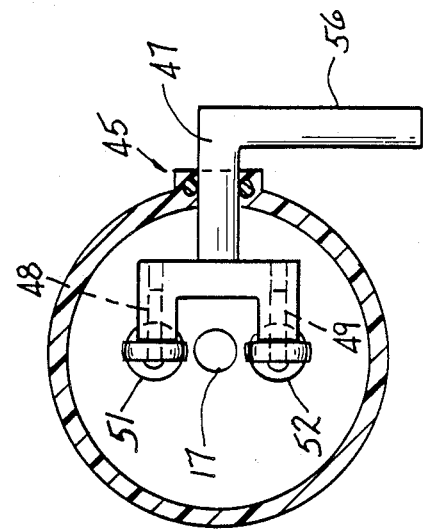
FIG. 4 is a vertical section of FIG. 3 in the plane of the line 4—4 as viewed in the direction of the arrows.

Referring to FIGS. 3 and 4, note that the control handle unit 12 includes a power means defining a link 46 pivoted to the handle housing at 45 by crank pin 47. The link 46, in turn, is connected pivotally, by pins 48 and 49, to a pair of rods (push-pull rods) 51 and 52, respectively, operable to reciprocate as indicated by the arrows 53 and 54 in response to operation of crank arm 56.

As is most apparent in FIG. 2, the operation of the crank arm (usually manually) to move push rods 51 and 52 from the equilibrium position of FIG. 3 to the actuated position of FIG. 2 moves the rods 51 and 52 into minimal area, surface contact with the crosshead 32 (and/or the beads 33-34). The language "minimal areal surface contact" is intended to denote that there is no positive connection such as by interlocking elements, magnetism, interrupted threads or the like, between the rods 51-52 and the crosshead or rocker arm 32.

It is well to note that although the crank arm 56 can be operated manually it is entirely within the spirit and scope of the invention that the link 46 be operated and powered electrically, such as by a solenoid or a small electric motor.

As can be seen in FIG. 2, operation of the push rods 51 and 52 in the manner described is effective to actuate the control wires 28 and 29 to deflect the distal end 19 of the shaft 13 in a manner and for purposes that are well known in the endoscope art.

Note further that each outlet or opening in the control handle unit is sealed by O-rings to make the interior of the handle watertight as indicated by the reference numerals 57, 58, 59 and 61.

Expanding upon on the nature of the operational contact between the push rods and the rocker arm 32, it is to be noted that the placement of critical elements of the shaft flexure means such as the rocker arm 32 in the shaft unit and the push pull rods 51 and 52 of the power means within the control handle unit makes it possible to provide a dependable method for articulating the distal end of an endoscope having a disposable shaft which one can dispose of economically.

Stated otherwise the expensive elements of the invention are within the control handle unit while the elements of the disposable shaft are relatively inexpensive.

It is anticipated that this invention will find utility in endoscopes that are used industrially and in veterinary situations as well as in medical applications.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An endoscope having a disposable shaft comprising:
    a control handle,
    a separable, disposable, flexible shaft having a distal end and a proximal end,
    connector means for connecting the control handle and the shaft releasably,
    movable means incorporated in said shaft for flexing the distal end of the shaft, and,
    power means in said handle for making a separable driving connection with said movable means for articulating the distal end of said shaft.

2. The endoscope of claim 1 in which the control handle is provided with a plurality of seal means whereby the control handle can be immersed in fluid without contaminating the interior of the control handle.

3. The endoscope of claim 1 in which said power means defines a pair of pivotally mounted push rods.

4. The endoscope of claim 1 in which the movable means includes strand means.

5. The endoscope of claim 3 in which the power means includes a crank arm on the exterior of the control handle for operating the push rods in reciprocating fashion.

6. A disposable member for an endoscope comprising:
    an elongated, flexible shaft means having a distal end and a proximal end,
    strand means disposed in said shaft means operable to deflect the distal end of the shaft,
    a first end of said strand means terminating at said distal end and a second end of said strand means terminating at said proximal end,
    movable means within said shaft means at the proximal end of said shaft means making a fixed connection with the strand means whereby said movable means is operable to move said strand means to deflect the distal end of said shaft means.

7. The flexible shaft means of claim 6 wherein the movable means includes a rocker arm fulcrumed about a pivot fixed to said shaft means.

8. In combination, the shaft means of claim 7 plus a control handle connector means for making a releasable connection between the shaft means and the control handle, said rocker arm being operable to pivot in response to reciprocatory motion developed in said control handle.

9. An endoscope comprising:
    a control handle means,
    a flexible shaft means,
    connector means for connecting the shaft means and the control handle means releasably,
    articulation means within said shaft means, and,
    power means in said handle means for driving said articulation means, said power means and said articulation means making areal, surface contact when the handle means and the shaft means are connected.

10. The endoscope of claim 9 in which the handle means is fluid tight.

11. The endoscope of claim 9 in which the power means defines a push-pull mechanism.

12. The endoscope of claim 9 in which the power means is operable manually.

13. The endoscope of claim 11 in which the push-pull mechanism includes at least two elongated rods mounted pivotally to a movable link means.

14. The endoscope of claim 13 in which the link means is connected to a crank means for moving said link means.

15. The endoscope of claim 14 in which the crank means includes a crank arm on the exterior of said control handle means.

16. In an endoscope having a control handle unit and a separable, disposable, flexible shaft unit, a method for making the disposable unit articulable while preserving the disposable character of the shaft unit comprising:
 providing a control handle unit;
 providing a disposable, flexible shaft unit separable from said control handle unit,
 placing shaft flexure means in the shaft unit,
 placing power means in the control handle unit for driving the shaft flexure means, and,
 positioning the power means and the shaft flexure means in their respective units so that when the units are connected the power means contacts the flexure means whereby operation of the power means is effective to drive the shaft flexure means.

17. The method of claim 16 in which the control handle unit includes a pair of reciprocating push rods and the shaft unit includes a rocker arm whereby the push rods are operable to contact and move the rocker arm.

18. The method of claim 17 in which the shaft unit includes at least two flexible strands each terminating at one end at the rocker arm and terminating at the opposite end at a distal end of the shaft unit whereby movement of the rocker arm is operable to flex the distal end of the shaft unit.

* * * * *

REEXAMINATION CERTIFICATE (2168th)
United States Patent [19]
Siegmund

[11] B1 4,919,112
[45] Certificate Issued Dec. 28, 1993

[54] LOW-COST SEMI-DISPOSABLE ENDOSCOPE

[75] Inventor: Walter P. Siegmund, Windham, Conn.

[73] Assignee: Schott Fiber Optics, Southbridge, Mass.

Reexamination Request:
No. 90/002,414, Aug. 23, 1991

Reexamination Certificate for:
Patent No.: 4,919,112
Issued: Apr. 24, 1990
Appl. No.: 334,335
Filed: Apr. 7, 1989

[51] Int. Cl.⁵ ............................................. A61B 1/00
[52] U.S. Cl. ........................................... 128/4; 128/6
[58] Field of Search ................................. 128/4, 6, 7

[56] References Cited

U.S. PATENT DOCUMENTS

| | | | |
|---|---|---|---|
| 3,091,235 | 5/1963 | Richards | 128/6 |
| 3,572,325 | 3/1971 | Bazell et al. | 128/6 |
| 3,788,304 | 1/1974 | Takahashi | 128/6 |
| 3,892,228 | 7/1975 | Mitsui | 128/4 |
| 3,913,568 | 10/1975 | Carpenter | 128/11 |
| 4,290,421 | 9/1981 | Siegmund | 128/6 |
| 4,534,339 | 8/1985 | Collins et al. | 128/6 |
| 4,911,148 | 3/1990 | Sosnowski et al. | 128/6 |

*Primary Examiner*—William H. Grieb

[57] ABSTRACT

An endoscope is disclosed having a separable, disposable shaft where a push-pull mechanism, housed in liquid tight fashion in a control handle unit, is operable to actuate a shaft flexure means within the shaft effective deflect the distal end of the shaft.

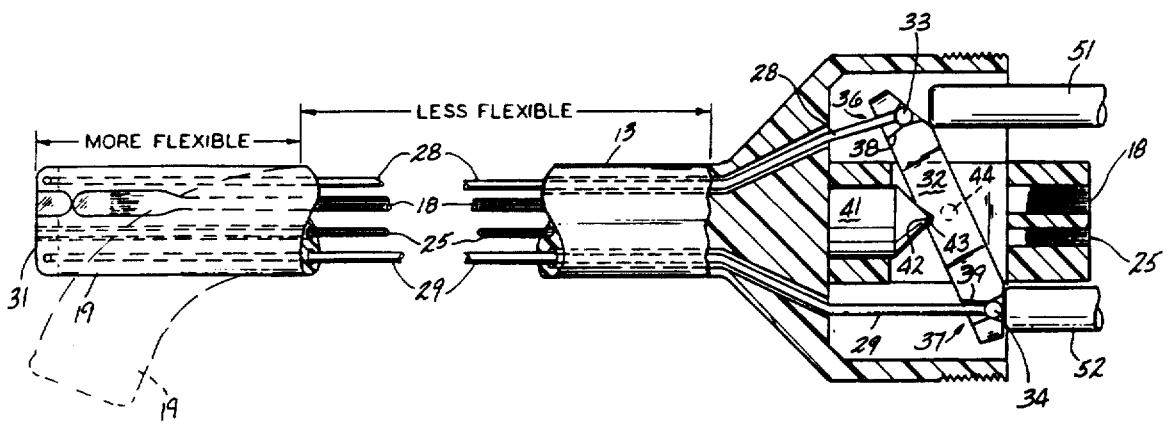

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 14–16:
In addition, it is desirable to provide means in the shaft [operable] *operable* via the [control] *control* handle unit to flex the shaft, in particular, the distal end of the shaft.

Column 1, lines 41–46:
A further feature of the invention is the placement of power means in the handle unit and the placement of shaft flexure means in the shaft unit so that mere areal, surface contact between elements of the power means and the shaft [flexure] *flexure* means is adequate to complete a driving connection.

Column 2, lines 21–23:
FIG. 1 is a sectional view of a portion of an [1U] endoscope [showinq] *showing* a disposable, flexible shaft unit connected to a control handle unit;

Column 2, lines 54–58:
The shaft may take the form of an extrusion. It is also desireable to fabricate a portion of the shaft unit, near the [diatal] *distal* end 19, of a material that is more flexible than the flexibility of the main body of the shaft (as indicated in FIG. 2) to facilitate deflection of the distal end.

AS A RESULT OF REEXAMINATION, IT HAS BEEN DETERMINED THAT:

Claims 1, 3, 6, 7, 9, 11, 13 and 16 are cancelled.

Claims 2, 4, 5, 8, 10, 12, 14, 17 and 18 are determined to be patentable as amended.

Claim 15, dependent on an amended claim, is determined to be patentable.

New claims 19-21 are added and determined to be patentable.

2. The endoscope of claim [1] *19* in which the control handle is provided with a plurality of seal means whereby the control handle can be immersed in fluid without contaminating the interior of the control handle.

4. The endoscope of claim [1] *19* in which the movable means includes strand means.

5. The endoscope of claim [3] *19* in which the power means includes a crank arm on the exterior of the control handle for operating the push rods in reciprocating fashion.

8. In combination, the shaft means of claim [7] *20* plus a control handle connector means for making a releasable connection between the shaft means and the control handle, said rocker arm being operable to pivot in response to reciprocatory motion developed in said control handle.

10. The endoscope of claim [9] *20* in which the handle means is fluid tight.

12. The endoscope of claim [9] *20* in which the power means is operable manually.

14. The endoscope of claim [13] *21* in which the link means is connected to a crank means for moving said link means.

17. The method of claim [16] *21* in which the control handle unit includes a pair of reciprocating push rods and the shaft unit includes a rocker arm whereby the push rods are operable to contact and move the rocker arm.

18. The method of claim 17 in which the shaft [unit] *flexure means* includes at least two flexible strands each terminating at one end at the rocker arm and terminating at the opposite end at a distal end of the shaft unit whereby movement of the rocker arm is operable to flex the distal end of the shaft unit.

*19. An endoscope having a diposable shaft comprising:*
*a control handle,*
*a separable, disposable, flexible shaft having a distal end and a proximal end,*
*connector means for connecting the control handle and the shaft releasably,*
*movable means incorporated in said shaft for flexing the distal end of the shaft, and,*
*power means in said handle for making a separable driving connection with said movable means for articulating the distal end of said shaft, said power means defining link means and a pair of push rods, said link means being pivotally connected to said push rods.*

*20. A disposable member for an endoscope comprising:*
*an elongated, flexible shaft having a distal end and a proximal end,*
*strand means disposed in said shaft means operable to deflect the distal end of the shaft,*
*a first end of said strand means terminating at said distal end and a second end of said strand means terminating at said proximal end,*
*movable means within said shaft means at the proximal end of said shaft means making a fixed connection with the strand means whereby said movable means is operable to move said strand means to deflect the distal end of said shaft means, said movable means comprising a rocker arm fulcrumed about a pivot fixed to said shaft means.*

*21. In an endoscope having a control handle unit and a separable, disposable, flexible shaft unit, a method for making the disposable unit articulable while preserving the disposable character of the shaft unit comprising:*
*providing a control handle unit;*
*providing a disposable, flexible shaft unit separable from said control handle unit,*
*placing shaft flexure means in the shaft unit,*
*placing power means including movable link means and at least two elongated rods mounted pivotally to the link means in the control handle unit for driving the shaft flexure means, and,*
*positioning the power means and the shaft flexure means in their respective units so that when the units are connected the power means contacts the flexure means whereby operation of the power means is effective to drive the shaft flexure means.*

* * * * *